US012622942B2

(12) United States Patent
Tseng et al.

(10) Patent No.: US 12,622,942 B2
(45) Date of Patent: May 12, 2026

(54) METHOD FOR TREATING CORONAVIRUS INFECTIOUS DISEASE AND COMPLICATED SEVERE COMA, ULTRA-LOW BLOOD OXYGEN, MORIBUND DISEASE THEREOF

(71) Applicant: Hsuan-Ching Tseng, New Taipei City (TW)

(72) Inventors: Hsuan-Ching Tseng, New Taipei City (TW); Da-Tong Ju, Taipei City (TW); Chi-Tun Tang, Taipei City (TW); Tung-Han Tsai, Kaohsiung City (TW); Tsai-Wang Huang, Taipei City (TW); Ming-Chin Ku, Taipei City (TW); Tzu-Li Lin, Taipei City (TW); Kun-Cheng Lin, New Taipei City (TW); Chen-Yu Lee, Taipei City (TW)

(73) Assignee: Tseng Hsuan-Ching, New Taipei City (TW)

( * ) Notice: Subject to any disclaimer, the term of this patent is extended or adjusted under 35 U.S.C. 154(b) by 699 days.

(21) Appl. No.: 17/959,449

(22) Filed: Oct. 4, 2022

(65) Prior Publication Data

US 2024/0108670 A1 Apr. 4, 2024

(51) Int. Cl.

| | |
|---|---|
| *A61K 36/17* | (2006.01) |
| *A61K 33/06* | (2006.01) |
| *A61K 36/076* | (2006.01) |
| *A61K 36/258* | (2006.01) |
| *A61K 36/28* | (2006.01) |
| *A61K 36/284* | (2006.01) |
| *A61K 36/31* | (2006.01) |
| *A61K 36/484* | (2006.01) |
| *A61K 36/539* | (2006.01) |
| *A61K 36/59* | (2006.01) |
| *A61K 36/708* | (2006.01) |
| *A61K 36/736* | (2006.01) |
| *A61K 36/884* | (2006.01) |
| *A61K 36/8888* | (2006.01) |
| *A61P 31/14* | (2006.01) |

(52) U.S. Cl.
CPC ............ *A61K 36/17* (2013.01); *A61K 36/076* (2013.01); *A61K 36/284* (2013.01); *A61K 36/31* (2013.01); *A61K 36/484* (2013.01);

*A61K 36/539* (2013.01); *A61K 36/59* (2013.01); *A61K 36/708* (2013.01); *A61K 36/884* (2013.01); *A61K 36/8888* (2013.01); *A61P 31/14* (2018.01); *A61K 33/06* (2013.01); *A61K 36/258* (2013.01); *A61K 36/28* (2013.01); *A61K 36/736* (2013.01)

(58) Field of Classification Search
None
See application file for complete search history.

(56) References Cited

FOREIGN PATENT DOCUMENTS

CN 111658752 A * 9/2020 ............. A61K 36/17

OTHER PUBLICATIONS

Ugwah-Oguejiofor, C.J. & Adebisi, I.M., Potential Medicinal Plant Remedies and Their Possible Mechanisms Against Covid-19: A Review, Ife Journal of Science vol. 23, No. 1 (2021) (Year: 2021).*
Sumarlina, E.S.N., et al., Family Medicine Plants in the Covid-19 Pandemic Based on Ancient Sundanese Manuscripts, Advances in Social Science, Education and Humanities Research, vol. 644, (2021) (Year: 2021).*
Machine translation (2025) of CN 111658752 A.*
Tseng, Hsuan-Ching, Huang, Tsai-Wang, Lee, Chen-Yu, Ju, Da-Tong, Tang, Chi-Tun, Liu, Wei-Hsiu, Report on interventional treatment of Lee Chen-Yu TCM physician for a near-death case in the Covid intensive care unit, The Journal of Chinese-Western Neurology Medicine.

* cited by examiner

*Primary Examiner* — H. Sarah Park
(74) *Attorney, Agent, or Firm* — BACON & THOMAS, PLLC

(57) ABSTRACT

The present invention relates to a method for treating a coronavirus infectious disease and a complication thereof, including: administering a Chinese medicine composition to a subject in need thereof; wherein, the Chinese medicine composition is an extract of a first mixture including *Ephedra sinica, Armeniacae Semen amarum, Glycyrrhizae radix et rhizoma, Gypsum fibrosum, Descurainiea semen, stephaniae Tetrandrae radix, Scutellariae radix, Poria, rhizoma alismatis, Polyporus umbellatus, Atractylodis rhizoma, Asteris radix et rhizoma, Tussilago farfara, Pinelliae rhizoma,* and *Rhei radix et rhizoma.*

7 Claims, No Drawings

METHOD FOR TREATING CORONAVIRUS INFECTIOUS DISEASE AND COMPLICATED SEVERE COMA, ULTRA-LOW BLOOD OXYGEN, MORIBUND DISEASE THEREOF

BACKGROUND OF THE INVENTION

1. Field of the Invention

The present invention relates to a method for treating a coronavirus infectious disease and a complication thereof, and, more particularly, to a method for treating acute respiratory syndrome coronavirus 2 (SARS-CoV-2).

2. Description of Related Art

Traditional Chinese medicine has gradually attracted attention in recent years due to the potential of Chinese medicine for coronavirus infectious diseases and complications thereof. The principle of applying Chinese medicine is based on the practice of traditional Chinese medicine theory.

The novel coronavirus broke out in Wuhan at the end of 2019, and then spread to countries around the world. In 2020, the International Committee on Taxonomy of Viruses officially named it severe acute respiratory syndrome coronavirus 2 (SARS-CoV-2), and the World Health Organization (WHO) also officially named the disease caused by such virus as COVID-19.

Most of the COVID-19 patients are asymptomatic or mildly symptomatic, but some patients will rapidly develop into severe illness after infection. Such disease is life-threatening and has a high mortality rate, so it is extremely difficult to be treated clinically. However, there is no specific medicine for COVED-19 patients nowadays, and supportive care is applied to the patient with the help of the medical personal mainly. The supportive care refers to a treatment for controlling and alleviating the complications or drug side effects with the purpose of preventing the patient from excessive pain until the patient produces antibody and recovers.

Therefore, it is desirable to provide a new therapeutic drug or treat lent method for the patient infected with the coronavirus at present, to alleviate a coronavirus infectious disease and a complication thereof.

SUMMARY OF THE INVENTION

A first aspect of the present invention relates to a Chinese medicine composition for treating a cornavirus infectious disease and a complication thereof, wherein the Chinese medicine composition comprises an extract of a first mixture comprising *Ephedra sinica, Armeniacae Semen amarum, Glycyrrhizae radix* et *rhizoma, Gypsum fibrosum, Descurainiea semen, stephaniae Tetrandrae radix, Scutellariae radix, Poria, rhizoma alismatis, Polyporus umbellatus, Atractylodis rhizoma, Asteris radix* et *rhizoma, Tussilago farfara, Pinelliae rhizoma*, and *Rhei radix* et *rhizoma*.

The first mixture of the first mixture of the present invention nay comprise 2-4 parts by weight of *Ephedra sinica*, 7-9 parts by weight of *Armeniacae Semen amarum*, 4-6 parts by weight of *Glycyrrhizae radix* et *rhizoma*, 7-9 parts by weight of *Gypsum fibrosum*, 7-9 parts by weight of *Descurainiea semen*, 4-6 parts by weight of *stephaniae Tetrandrae radix*, 7-9 parts by weight of *Scutellariae radix*, 7-9 parts by weight of *Poria*, 3-5 parts by weight of *rhizoma alismatis*, 3-5 parts by weight of *Polyporus umbellatus*, 3-5 parts by weight of *Atractylodis rhizoma*, 3-7 parts by weight of *Asteris radix* et *rhizoma*, 3-7 parts by weight of *Tussilago farfara*, 3-5 parts by weight of *Pinelliae rhizoma*, and 2-4 parts by weight of *Rhei radix* et *rhizoma*.

Said first mixture of the present invention may further comprise at least one ingredient selected from—the group consisting of *Ginseng radix* et *rhizoma* and *Anredera cordifolia*. In one embodiment of the present invention, the first mixture may further comprise at least one ingredient selected from the group consisting of 1-3 parts by weight of *Ginseng radix* et *rhizoma* and 1-3 parts by weight of *Anredera cordifolia*.

Said mixture may further comprise *Ginseng radix* et *rhizoma* and *Anredera cordifolia*. In one embodiment of the present invention, the first mixture may further comprise 1-3 parts by weight of *Ginseng radix* et *rhizoma* and 1-3 parts by weight of *Anredera cordifolia*.

A second aspect of the present invention relates to a Chinese medicine composition for treating a coronavirus infectious disease and a complication thereof, wherein the Chinese medicine composition comprises an extract of a first mixture comprising *Ephedra sinica, Armeniacae Semen amarum, Scutellariae radix, Poria, Atractylodis rhizoma, Asteris radix* et *rhizoma, Tussilago farfara, Pinelliae rhizoma, Ginseng radix* et *rhizoma, Anredera cordifolia, Salviae miltiorrhizae radix* et *rhizoma, radix glycyrrhizae, Aucklandiae radix, Amomi fructus, Schisandra chinensis, Citri reticulatae pericarpium, Ginkgo semen, Dioscoreae rhizoma, Pimenta officinalis, Zingiberis rhizoma*, and *Aconiti lateralis radix praeparata*.

The first mixture of the second aspect of the present invention gay comprise 2-4 parts by weight of 2-4 parts by weight of *Ephedra sinica*, 3-5 parts by weight of *Armeniacae Semen amarum*, 7-9 parts by weight of *Scutellariae radix*, 2-4 parts by weight of *Poria*, 2-4 parts by weight of *Atractylodis rhizoma*, 3-5 parts by weight of *Asteris radix* et *rhizoma*, 3-5 parts by weight of *Tussilago farfara*, 3-5 parts by weight of *Pinelliae rhizoma*, 2-4 parts by weight of *Ginseng radix* el *rhizoma*, 2-4 parts by weight of *Anredera cordifolia*, 2-4 parts by weight of *Salviae Miltiorrhizae radix* et *rhizoma*, 2-4 parts by weight of *radix glycyrrhizae*, 2-4 parts by weight of *Aucklandiae radix*, 2-4 parts by, weight of *Amomi fructus*, 2-4 parts by weight of *Schisandra chinensis*, 3-5 parts by weight of *Citri Reticulatae pericarpium*, 3-5 parts by weight of *Ginkgo semen*, 4-6 parts by weight of *Dioscoreae rhizoma*, 4-6 parts by weight of *Pimenta officinalis*, 4-6 parts by weight of *Zingiberis rhizoma*, and 4-6 parts by weight of *Aconiti lateralis radix praeparata*.

The present invention further provides a method for treating a coronavirus infectious disease and a complication thereof, comprising: administering the Chinese medicine composition above to a subject in need thereof. In particular, an effective dose of the Chinese medicine composition is administered to a subject in need thereof.

The Chinese medicine composition of the present invention may be prepared by the Mowing steps: providing said first mixture; mixing the first mixture with rater to form a second mixture; heating the second mixture to obtain a crude extract; and filtering the crude extract and keep a liquid extract to obtain the Chinese medicine composition.

In the present invention, the part by weight of the first mixture is 2.5-5 gram per part, preferably 3-4 gram per part, more preferably 3.75 gram per part. However, the present invention is not limited thereto.

In the present invention, the coronavirus may be severe acute respiratory syndrome coronavirus 2 (SARS-CoV-2).

In the present invention, the term "treat" or "treatment" used herein refers to administer a Chinese medicine composition of the present invention to a subject in need thereof thereby inhibiting, curing, improving, healing, ameliorating, alleviating, or changing or affecting the tendency of disease or conditions. For instance, the method of the present invention may be used to inhibit division, replication, proliferation, invasion or transmigration of coronavirus.

In the present invention, the term "effective amount" used herein refers to a necessary dose leading to expected therapeutic effects in a subject treated, and it may be changed depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention is not restrictive of the method for decocting Chinese medicine, and it can be carried out in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined by the following definition. In the present invention, the singular term and "the", may refer to one or more object(s), unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

In the following preparation examples, the part by weight is 3.75 gram per part.

Preparation Example 1

Three parts by weight of *Ephedra sinica*, 8 parts by weight of *Armeniacae Semen amarum*, 5 parts by weight of *Glycyrrhizae radix* et *rhizoma*, 8 parts by weight of *Gypsum fibrosum*, 8 parts by weight of *Descurainiea semen*, 5 parts by weight of *Stephaniae Tetrandrae radix*, 8 parts by weight of *Scutellariae radix*, 8 parts by weight of *Poria*, 4 parts by weight of *rhizoma alismatis*, 4 parts by weight of *Polyporus umbellatus*, 4 parts by weight of *Atractylodis rhizoma*, 4 parts by weight of *Asteris radix* et *rhizoma*, 4 parts by weight of *Tussilago farfara*, 4 parts by weight of *Pinelliae rhizoma*, and 3 parts by weight of *Rhei radix* et *rhizoma* were provided to form a mixture, added with 1500 parts by weight of water, and heated for 1 hour to form a crude extract of about 400 parts by weight. The crude extract was filtered and the filtrate was collected to obtain a first extract of the present embodiment. In addition, *Descurainiea semen*, *Stephaniae Tetrandrae radix*, *Poria*, *rhizoma alismatis*, *Polyporus umbellatus*, *Atractylodis rhizoma*, *Pinelliae rhizoma* were used to alleviate pleural effusion, allowing the mucus and water in the pleura or trachea to be diluted, exuded and exuded back. Furthermore, *Gypsum fibrosum* and *Scutellariae radix* were used to reduce inflammation, suppress immune hyperactivity, and avoid inflammation of the trachea and throat. Moreover, *Rhei radix* et *rhizoma* was used to reduce abdominal pressure and dissolve thrombus. The effects of the same ingredients would not be described hereinafter.

Preparation Example 2

The present preparation example was similar to Preparation Example 1, except that the mixture was further added with 2 parts by weight of *Asteris radix* et *rhizoma*, 2 parts b weight of *Tussilago Farfara*, 1.6 parts by weight of *Ginseng radix* et *rhizoma*, 1 parts by weight of *Anredera Cordifolia*. Then, the extraction process thereof was performied according to an extraction process similar to Preparation 1, thereby obtaining a second extract of the present preparation example. The abilities of blood exchange and oxygen exchange were improved by *Ginseng radix* et *rhizoma and Anredera cordifolia*, wherein *Ginseng radix* et *rhizoma* was used to increase the oxygen level in blood. In addition, the dosages of *Asteris radix* et *rhizoma* and *Tussilago farfara* were increased for improving and discharge the sick sputum. The effects of the same ingredients would not be described hereinafter.

Preparation Example 3

Three parts by weight of *Ephedra sinica*, 4 parts by weight of *Armeniacae Semen amarum*, 8 parts by weight of *Scutellariae radix*, 3 parts by weight of *Poria*, 3 parts by weight of *Atractylodis rhizoma*, 4 parts by weight of *Asteris radix* et *rhizoma*, 4 parts by weight of *Tussilago farfara*, 4 parts by weight of *Pinelliae rhizoma*, 3 parts by weight of *Ginseng radix* et *rhizoma*, 3 parts by weight of *Anredera cordifolia*, 3 parts by weight of *Salviae Miltiorrhizae radix* et *rhizoma*, 3 parts by weight of *radix glycyrrhizae*, 3 parts by weight of *Aucklandiae radix*, 3 parts by weight of *Amomi fructus*, 3 parts by weight of *Schisandra chinensis*, 4 parts by weight of *Citri reticulatae pericarpium*, 4 parts by weight of *Ginkgo semen*, 5 parts by weight of *Dioscoreae rhizoma*, 5 parts by weight of *Pimenta officinalis*, 5 parts by weight of *Zingiberis rhizoma*, and 5 parts by weight of *Aconiti lateralis radix praeparata* were provided to form a mixture. Then, the extraction process thereof was performed according to an extraction process similar to Preparation 1, thereby obtaining a third extract of the present preparation example. Furthermore, *Ginkgo semen* and *Schisandra chinensis* could improve cardiopulmonary function and had the ability to stabilize or increase blood oxygen level. In addition to the above functions, *Schisandra chinensis* could also avoid the symptoms of drug-induced hepatitis or liver failure.

Example 1

The patient of Example 1 suffered from COVID-19 with multiple pulmonary ground glass opacities in both lungs, and the chest X-ray showed opacity.

A treatment of the present embodiment applied to the patient of Example 1 was described below. A daily dose of the first extract of Preparation Example 1 was administered to the patient every day from the first day; wherein the daily dose of the first extract was divided into aliquots for ter in die administration. A follow-up report indicated that pulmonary ground glass opacities were significantly alleviated, and the alveolar infiltrates were significantly improved.

Example 2

The patient of Example 2 suffered from COVID-19 with pleural effusion.

A treatment of the present embodiment applied to the patient of Example 2 was described below. A daily dose of the first extract of Preparation Example 1 was administered to the patient every day from the first day, wherein the daily dose of the first extract was divided into aliquots for ter in die administration. A follow-up report indicated that pleural effusion was in complete remission, and the mucus and water in the pleura and trachea could exude and exude back normally.

Example 3

The patient of Example 3 suffered from COVID-19 with pleural effusion, and complicated by anemia concurrently.

A treatment of the present embodiment applied to the patient of Example 3 was described below, A daily dose of the first extract of Preparation Example 1 was administered to the patient every day from the first day wherein the daily dose of the first extract was divided into aliquots for ter in die administration. A follow-up report indicated that pleural effusion was in complete remission, and the complication was in complete remission.

Example 4

The patient of Example 4 suffered from COVID-19 with pleural effusion, and the patient's blood oxygen was below 80 mmHg (the normal value of blood oxygen was higher than 95 mmHg).

A treatment of the present embodiment applied to the patient of Example 4 was described below. A daily dose of the first extract of Preparation Example 1 was administered to the patient every day from the first day; wherein the daily dose of the first extract was divided into aliquots for ter in die administration. A follow-up report indicated that pleural effusion was in complete remission, the blood oxygen was increased to higher than 85 mmHg, and the blood circulation and blood oxygen level were improved.

Example 5

The patient of Example 5 suffered from COVID-19 with pleural effusion, the blood oxygen was below 80 mmHg, and the amount of oxygen used for intubation was reduced by 50%.

A treatment of the present embodiment applied to the patient of Example 5 was described below. A daily dose of the second extract of Preparation Example 2 was administered to the patient every day from the first day, wherein the daily dose of the first extract was divided into aliquots for ter in die administration. A follow-up report indicated that pleural effusion was in complete remission, and the blood oxygen was increased to higher than 95 mmHg.

Example 6

The patient of Example 6 suffered from COVID-19 with pleural effusion, blood oxygen was below 80 mmHg, and was complicated by hypoxemia.

A treatment of the present embodiment applied to the patient of Example 6 was described below A daily dose of the second extract of Preparation Example 2 was administered to the patient every day from the first day; wherein the daily dose of the first extract was divided into aliquots for ter in die administration. A follow-up report indicated that pleural effusion was in complete remission, the blood oxygen was increased to higher than 95 mmHg, and the complication was in complete remission.

Example 7

The patient of Example 7 suffered from COVID-19 with pleural effusion, and was complicated by hypokalemia and hypoxemia concurrently.

A treatment of the present embodiment applied to the patient of Example 7 was described below. A daily dose of the third extract of Preparation Example 3 was administered to the patient every day from the first day, wherein the daily dose of the first extract was divided into aliquots for ter in die administration. A follow-up report indicated that pleural effusion was in complete remission, and the complications were in complete remission.

Example 8

The patient of Example 8 suffered from COVID-19 with pleural effusion, blood oxygen was below 80 mmHg, and GOP and GPT thereof were 38 U/L (the normal value of GOP was below 40 U/L) and 79 U/L (the normal value of GPT was below 40 U/L), respectively.

A treatment of the present embodiment applied to the patient of Example 8 was described below. A daily dose of the third extract of Preparation Example 3 was administered to the patient every day from the first wherein the daily dose of the first extract was divided into aliquots for ter in die administration. A follow-up report indicated that pleural effusion was in complete remission, blood oxygen was increased to higher than 95 mmHg, and liver injury indicators were back to normal.

Example 9

The patient of Example 9 suffered from COVID-19 with pleural effusion, the blood oxygen was once as low as 39.5 mmHg, and the foot embolism thereof showed black.

A treatment of the present embodiment applied to the patient of Example 9 was described below. A daily dose of the third extract of Preparation Example 3 was administered to the patient every day from the first day, wherein the daily dose of the first extract was divided into aliquots for ter in die administration. A follow-up report indicated that pleural effusion was in complete remission, blood oxygen was increased to higher than 95 mmHg, and the foot embolism was in complete remission.

Although the present invention has been explained in relation to its preferred embodiment, it is to be understood that many other possible modifications and variations can be made without departing from the spirit and scope of the invention as hereinafter claimed.

What is claimed is:

1. A method for treating a coronavirus infectious disease and a complication thereof, comprising: administering a Chinese medicine composition to a subject in need thereof, wherein, the Chinese medicine composition is an extract of a first mixture consisting of 2-4 parts by weight of *Ephedra sinica,* 7-9 parts by weight of *Armeniacae semen amarum,* 4-6 parts by weight of *Glycyrrhizae radix* et *rhizoma,* 7-9 parts by weight of *Gypsum fibrosum,* 7-9 parts by weight of *Descurainiea semen,* 4-6 parts by weight of *Stephaniae tetrandrae radix,* 7-9 parts by weight of *Scutellariae radix,* 7-9 parts by weight of *Poria,* 3-5 parts by weight of *Rhizoma alismatis,* 3-5 parts by weight of *Polyporus umbellatus,* 3-5 parts by weight of *Atractylodis rhizoma,* 3-7 parts by weight of *Asteris radix* et *rhizoma,* 3-7 parts by weight of *Tussilago farfara,* 3-5 parts by weight of *Pinelliae rhizoma,* 2-4 parts by weight of *Rhei radix* et *rhizome,* 0-3 parts by weight of *Ginseng radix* et *rhizome* and 0-3 parts by weight of *Anredera cordifolia.*

2. The method of claim 1, wherein the Chinese medicine composition is prepared by the following steps:

providing the first mixture;

mixing the first mixture with water to form a second mixture;

heating the second mixture to obtain a crude extract; and filtering the crude extract and keeping a filtrate to obtain the Chinese medicine composition.

3. The method of claim 1, wherein the first mixture consists of 2-4 parts by weight of *Ephedra sinica,* 7-9 parts by weight of *Armeniacae semen amarum,* 4-6 parts by weight of *Glycyrrhizae radix* et *rhizoma,* 7-9 parts by weight of *Gypsum fibrosum,* 7-9 parts by weight of *Descurainiea semen,* 4-6 parts by weight of *Stephaniae tetrandrae radix,* 7-9 parts by weight of *Scutellariae radix,* 7-9 parts by weight of *Poria,* 3-5 parts by weight of *Rhizoma alismatis,* 3-5 parts by weight of *Polyporus umbellatus,* 3-5 parts by weight of *Atractylodis rhizoma,* 5-7 parts by weight of *Asteris radix* et *rhizoma,* 5-7 parts by weight of *Tussilago farfara,* 3-5 parts by weight of *Pinelliae rhizoma,* 2-4 parts by weight of *Rhei radix* et *rhizoma,* 1-3 parts by weight of *Ginseng radix* et *rhizoma* and 1-3 parts by weight of *Anredera cordifolia.*

4. The method of claim 1, wherein the coronavirus is severe acute respiratory syndrome coronavirus 2 (SARS-COV-2).

5. The method of claim 1, wherein the Chinese medicine composition is administered via oral administration or injection.

6. The method of claim 1, wherein the Chinese medicine composition further comprises pharmaceutically acceptable carrier, stabilizer, diluent, dispersant, suspending agents, thickening agent, excipient, or a combination thereof.

7. The method of claim 1, wherein the complication comprises low blood oxygen, wherein the low blood oxygen is defined as a blood oxygen below 80 mmHg.

* * * * *